(12) United States Patent
Gleave et al.

(10) Patent No.: US 9,205,102 B2
(45) Date of Patent: Dec. 8, 2015

(54) METHOD FOR TREATMENT OF CASTRATION-RESISTANT PROSTATE CANCER

(71) Applicant: The University of British Columbia, Vancouver (CA)

(72) Inventors: Martin E. Gleave, Vancouver (CA); Joseph Ischia, Victoria (AU)

(73) Assignee: The University of British Columbia, Vancouver (CA)

( * ) Notice: Subject to any disclaimer, the term of this patent is extended or adjusted under 35 U.S.C. 154(b) by 0 days.

(21) Appl. No.: 14/560,673

(22) Filed: Dec. 4, 2014

(65) Prior Publication Data

US 2015/0157656 A1    Jun. 11, 2015

Related U.S. Application Data

(60) Provisional application No. 61/913,085, filed on Dec. 6, 2013.

(51) Int. Cl.
| | | |
|---|---|---|
| *C12N 15/11* | (2006.01) | |
| *C07H 21/04* | (2006.01) | |
| *C07H 21/02* | (2006.01) | |
| *A61K 31/713* | (2006.01) | |
| *A61K 45/06* | (2006.01) | |
| *A61K 31/4166* | (2006.01) | |
| *A61K 31/712* | (2006.01) | |

(52) U.S. Cl.
CPC .......... *A61K 31/713* (2013.01); *A61K 31/4166* (2013.01); *A61K 31/712* (2013.01); *A61K 45/06* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,469,863 A | 9/1984 | Ts'o et al. |
| 4,476,301 A | 10/1984 | Imbach et al. |
| 4,587,044 A | 5/1986 | Miller et al. |
| 4,605,735 A | 8/1986 | Miyoshi et al. |
| 4,667,025 A | 5/1987 | Miyoshi et al. |
| 4,762,779 A | 8/1988 | Snitman |
| 4,789,737 A | 12/1988 | Miyoshi et al. |
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Huynh Dinh et al. |
| 4,876,335 A | 10/1989 | Yamane et al. |
| 4,904,582 A | 2/1990 | Tullis |
| 4,948,882 A | 8/1990 | Ruth |
| 4,958,013 A | 9/1990 | Letsinger |
| 4,981,957 A | 1/1991 | Lebleu et al. |
| 5,013,830 A | 5/1991 | Ohtsuka et al. |
| 5,023,243 A | 6/1991 | Tullis |
| 5,034,506 A | 7/1991 | Summerton et al. |
| 5,082,830 A | 1/1992 | Brakel et al. |
| 5,109,124 A | 4/1992 | Ramachandran et al. |
| 5,112,963 A | 5/1992 | Pieles et al. |
| 5,118,800 A | 6/1992 | Smith et al. |
| 5,118,802 A | 6/1992 | Smith et al. |
| 5,130,302 A | 7/1992 | Spielvogel et al. |
| 5,134,066 A | 7/1992 | Rogers et al. |
| 5,138,045 A | 8/1992 | Cook et al. |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,194,599 A | 3/1993 | Froehler et al. |
| 5,214,134 A | 5/1993 | Weis et al. |
| 5,214,136 A | 5/1993 | Lin et al. |
| 5,216,141 A | 6/1993 | Benner |
| 5,218,105 A | 6/1993 | Cook et al. |
| 5,220,007 A | 6/1993 | Pederson et al. |
| 5,235,033 A | 8/1993 | Summerton et al. |
| 5,245,022 A | 9/1993 | Weis et al. |
| 5,254,469 A | 10/1993 | Warren, III et al. |
| 5,256,775 A | 10/1993 | Froehler |
| 5,258,506 A | 11/1993 | Urdea et al. |
| 5,262,536 A | 11/1993 | Hobbs, Jr. |
| 5,264,423 A | 11/1993 | Cohen et al. |
| 5,264,562 A | 11/1993 | Matteucci |
| 5,264,564 A | 11/1993 | Matteucci |
| 5,272,250 A | 12/1993 | Spielvogel et al. |

(Continued)

FOREIGN PATENT DOCUMENTS

| | | |
|---|---|---|
| WO | 9307883 A1 | 4/1993 |
| WO | 9839352 A1 | 9/1998 |
| WO | 9914226 A2 | 3/1999 |

OTHER PUBLICATIONS

Carney, D. N. et al., Establishment and Identification of Small Cell Lung Cancer Cell Lines Having Classic and Variant Features1, Cancer Research, 1985, pp. 2913-2923, vol. 45.

(Continued)

*Primary Examiner* — Richard Schnizer
(74) *Attorney, Agent, or Firm* — Larson & Anderson, LLC (57) ABSTRACT

Castrate resistant prostate cancer cell lines exhibiting resistance to the androgen-receptor antagonist enzaluatamide overexpress one or both of IGFBP-2 or IGFBP-5 when compared to non-resistant cell lines. Oligonucleotides that target IGFBP-2 and IGFBP-5 can be used to overcome this resistance or as part of a treatment program when administered concurrently with the administration of androgen-receptor antagonist treatments.

24 Claims, 5 Drawing Sheets

(56) References Cited

U.S. PATENT DOCUMENTS

| | | |
|---|---|---|
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,317,098 A | 5/1994 | Shizuya et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,371,241 A | 12/1994 | Brush |
| 5,391,723 A | 2/1995 | Priest |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger |
| 5,432,272 A | 7/1995 | Benner |
| 5,434,257 A | 7/1995 | Matteucci et al. |
| 5,446,137 A | 8/1995 | Maag et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,486,603 A | 1/1996 | Buhr |
| 5,489,677 A | 2/1996 | Sanghvi et al. |
| 5,491,133 A | 2/1996 | Walder et al. |
| 5,502,177 A | 3/1996 | Matteucci et al. |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Van Ness et al. |
| 5,519,126 A | 5/1996 | Hecht |
| 5,519,134 A | 5/1996 | Acevedo et al. |
| 5,525,465 A | 6/1996 | Haralambidis et al. |
| 5,525,711 A | 6/1996 | Hawkins et al. |
| 5,527,899 A | 6/1996 | Froehler |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,541,313 A | 7/1996 | Ruth |
| 5,545,730 A | 8/1996 | Urdea et al. |
| 5,550,111 A | 8/1996 | Suhadolnik et al. |
| 5,552,538 A | 9/1996 | Urdea et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,552 A | 10/1996 | Magda et al. |
| 5,565,555 A | 10/1996 | Froehler et al. |
| 5,567,810 A | 10/1996 | Weis et al. |
| 5,567,811 A | 10/1996 | Misiura et al. |
| 5,571,799 A | 11/1996 | Tkachuk et al. |
| 5,574,142 A | 11/1996 | Meyer, Jr. et al. |
| 5,576,427 A | 11/1996 | Cook et al. |
| 5,578,717 A | 11/1996 | Urdea et al. |
| 5,578,718 A | 11/1996 | Cook et al. |
| 5,580,731 A | 12/1996 | Chang et al. |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,591,722 A | 1/1997 | Montgomery et al. |
| 5,594,121 A | 1/1997 | Froehler et al. |
| 5,595,726 A | 1/1997 | Magda et al. |
| 5,596,086 A | 1/1997 | Matteucci et al. |
| 5,596,091 A | 1/1997 | Switzer |
| 5,597,696 A | 1/1997 | Linn et al. |
| 5,597,909 A | 1/1997 | Urdea et al. |
| 5,599,923 A | 2/1997 | Sessler et al. |
| 5,599,928 A | 2/1997 | Hemmi et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci et al. |
| 5,652,355 A | 7/1997 | Metelev et al. |
| 5,652,356 A | 7/1997 | Agrawal |
| 5,658,873 A | 8/1997 | Bertsch-Frank et al. |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,688,941 A | 11/1997 | Cook et al. |
| 5,700,920 A | 12/1997 | Altmann et al. |
| 5,700,922 A | 12/1997 | Cook |
| 5,714,331 A | 2/1998 | Buchardt et al. |
| 5,719,262 A | 2/1998 | Buchardt et al. |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,747 A | 8/1998 | Schally et al. |
| 5,830,653 A | 11/1998 | Froehler et al. |
| 6,005,096 A | 12/1999 | Matteucci et al. |
| 6,268,490 B1 | 7/2001 | Imanishi et al. |
| 6,287,860 B1 | 9/2001 | Monia et al. |
| 6,656,730 B1 | 12/2003 | Manoharan |
| 6,770,748 B2 | 8/2004 | Imanishi et al. |
| 7,399,845 B2 | 7/2008 | Seth et al. |
| 7,547,684 B2 | 6/2009 | Seth et al. |
| 7,666,854 B2 | 2/2010 | Seth et al. |
| 7,928,082 B2 | 4/2011 | Gleave et al. |
| 7,973,017 B2 | 7/2011 | Gleave |
| 8,252,918 B2 | 8/2012 | Gleave et al. |
| 2003/0158143 A1* | 8/2003 | Gleave et al. ............... 514/44 |
| 2008/0274996 A1* | 11/2008 | Gleave et al. ............... 514/44 |

OTHER PUBLICATIONS

Clegg, N. J. et al., ARN-509: A Novel Antiandrogen for Prostate Cancer Treatment, Cancer Research, 2012, pp. 1494-1503, vol. 72, No. 6, Published Online First Jan. 20, 2012.

Hayward, S. W. et al., Establishment and Characterization of an Immortalized but Non-Transformed Human Prostate Epithelial Cell Line: BPH-1, in Vitro Cell. Dev. Biol. Anim, 1995, pp. 14-24, vol. 31a.

Kenski, D. M. et al., siRNA-optimized Modifications for Enhanced In Vivo Activity, Citation: Molecular Therapy-Nucleic Acids, 2012, 1 e5.

Korpal, M. et al., An F876L Mutation in Androgen Receptor Confers Genetic and Phenotypic Resistance to MDV3100 (Enzalutamide), Cancer Discovery, 2013, pp. 1030-1043, vol. 3, Published OnlineFirst Jul. 10, 2013.

Kuruma, H. et al., A Novel Antiandrogen, Compound 30, Suppresses Castration-Resistant and MDV3100-Resistant Prostate Cancer Growth In Vitro and In Vivo, Mol Cancer Ther, 2013, pp. 567-576, vol. 12, No. 5, Published OnlineFirst Mar. 14, 2013.

(56) References Cited

OTHER PUBLICATIONS

Li, J. J. et al., Rational Design and Synthesis of 4-((1 R,2R)-2-Hydroxycyclohexyl)-2(trifluoromethyl)benzonitrile (PF-998425), a Novel, Nonsteroidal Androgen Receptor Antagonist Devoid of Phototoxicity for Dermatological Indications, J. Med. Chem, 2008, pp. 7010-7014, vol. 51, Published on Web Oct. 16, 2008.

Matsumoto, H. et al., Cotargeting Androgen Receptor and Clusterin Delays Castrate-Resistant Prostate Cancer Progression by Inhibiting Adaptive Stress Response and AR Stability, Cancer Res, 2013, pp. 5206-5217, vol. 73, No. 16, Published OnlinFirst Jun. 20, 2013.

Nielsen, P. E. et al., Sequence-Selective Recognition of DNA by Strand Displacement with a Thymine-Substituted Polyamide, Science,1991, pp. 1497-1500, Vo. 254.

Thalmann, G. N. et al. Androgen-independent Cancer Progression and Bone Metastasis in the LNCaP Model of Human Prostate Cancer, Cancer Research, 1994, pp. 2577-2581, vol. 54.

Tran, C. et al., Development of a Second-Generation Antiandrogen for Treatment of Advanced Prostate Cancer, Science, 2009, pp. 787-790, vol. 324(5928).

\* cited by examiner

Three candidate sites with 100% homology between IGFBP-2 and IGFBP-5 mRNA.

```
                              OGX-225

IGFBP-5  Query: 887  gagctggtcaaggagccggctgcggctgctgcatgacctgcgccctggccgaggggcag  946
                         ||| ||   |||||||||||| ||||||||||  |  ||||| ||||||  ||  ||
IGFBP-2  Sbjct: 355  gagctcgtccgggagccggctgcggctgctgcggtgtgcgccggctggaggggcgag  414

IGFBP-5  Query: 947  tcgtgcggcgtctacacdgagcgctgcgccccaggggggctgcgctgc  991
                    | ||| ||||||||||||  |||||||||| |||| ||||||||||||
IGFBP-2  Sbjct: 415  gcgtgcggcgtctacacccccgcgctgcgccccagggggctgcgctgc  459
```

*Also has 100% homology with IGFBP-3 and TGF-B1

SEQUENCE LISTING

<160> NUMBER OF SEQ ID NOS: 15

<210> SEQ ID NO 1
<211> LENGTH: 20
<212> TYPE: DNA
<213> ORGANISM: Homo sapiens

<400> SEQUENCE: 1
cagcagccgc agcccggctc                                          20

```
<210> SEQ ID NO 2
<211> LENGTH: 20
<212> TYPE: DNA
<213> ORGANISM: Artificial Sequence
<220> FEATURE:
<223> OTHER INFORMATION: modified antisense sequence
<220> FEATURE:
<221> NAME/KEY: misc_feature
<222> LOCATION: (1)..(20)
<223> OTHER INFORMATION: phosphorothioate backbone
<220> FEATURE:
<221> NAME/KEY: modified_base
<222> LOCATION: (1)..(1)
<223> OTHER INFORMATION: m5c further modified with 2'MOE
<220> FEATURE:
<221> NAME/KEY: modified_base
<222> LOCATION: (2)..(2)
<223> OTHER INFORMATION: further modified with 2'MOE
<220> FEATURE:
<221> NAME/KEY: modified_base
<222> LOCATION: (3)..(3)
<223> OTHER INFORMATION: ribonucleoside further modified with 2'MOE
<220> FEATURE:
<221> NAME/KEY: modified_base
<222> LOCATION: (3)..(3)
<223> OTHER INFORMATION: m5c further modified with 2'-MOE
<220> FEATURE:
<221> NAME/KEY: modified_base
<222> LOCATION: (4)..(4)
<223> OTHER INFORMATION: m5c further modified with 2'-MOE
<220> FEATURE:
<221> NAME/KEY: modified_base
<222> LOCATION: (5)..(5)
<223> OTHER INFORMATION: ribonucleoside further modified with 2'-MOE
<220> FEATURE:
<221> NAME/KEY: modified_base
<222> LOCATION: (7)..(8)
<223> OTHER INFORMATION: 2'-deoxy-m5c
<220> FEATURE:
<221> NAME/KEY: modified_base
<222> LOCATION: (10)..(10)
<223> OTHER INFORMATION: 2'-deoxy-m5c
<220> FEATURE:
<221> NAME/KEY: modified_base
<222> LOCATION: (13)..(14)
<223> OTHER INFORMATION: 2'-deoxy-m5c
<220> FEATURE:
<221> NAME/KEY: modified_base
<222> LOCATION: (16)..(17)
<223> OTHER INFORMATION: ribonucleoside further modified with 2'MOE
<220> FEATURE:
<221> NAME/KEY: modified_base
<222> LOCATION: (18)..(18)
<223> OTHER INFORMATION: m5c further modified with 2'MOE
<220> FEATURE:
<221> NAME/KEY: modified_base
<222> LOCATION: (19)..(19)
<223> OTHER INFORMATION: t further modified with 2'MOE
<220> FEATURE:
<221> NAME/KEY: modified_base
<222> LOCATION: (20)..(20)
<223> OTHER INFORMATION: m5c further modified with 2'MOE

<400> SEQUENCE: 2
cagcagccgc agcccggcuc                                                 20

<210> SEQ ID NO 3
<211> LENGTH: 17
<212> TYPE: DNA
<213> ORGANISM: Homo sapiens

<400> SEQUENCE: 3
ggtgtagacg ccgcacg                                                    17
```

```
<210> SEQ ID NO 4
<211> LENGTH: 16
<212> TYPE: DNA
<213> ORGANISM: Homo sapiens

<400> SEQUENCE: 4
gcagcgcagc ccctgg                                                       16

<210> SEQ ID NO 5
<211> LENGTH: 22
<212> TYPE: DNA
<213> ORGANISM: Homo sapiens

<400> SEQUENCE: 5
gcagcagccg cagcccggct cc                                                22

<210> SEQ ID NO 6
<211> LENGTH: 18
<212> TYPE: DNA
<213> ORGANISM: Homo sapiens

<400> SEQUENCE: 6
agccgcagcc cggctcct                                                     18

<210> SEQ ID NO 7
<211> LENGTH: 18
<212> TYPE: DNA
<213> ORGANISM: Homo sapiens

<400> SEQUENCE: 7
agccgcagcc cggctcct                                                     18

<210> SEQ ID NO 8
<211> LENGTH: 20
<212> TYPE: DNA
<213> ORGANISM: Homo sapiens

<400> SEQUENCE: 8
gcagcagccg cagcccggct                                                   20

<210> SEQ ID NO 9
<211> LENGTH: 20
<212> TYPE: DNA
<213> ORGANISM: Homo sapiens

<400> SEQUENCE: 9
agcagccgca gcccggctcc                                                   20

<210> SEQ ID NO 10
<211> LENGTH: 21
<212> TYPE: DNA
<213> ORGANISM: Artificial Sequence
<220> FEATURE:
<223> OTHER INFORMATION: one strand RNAi for human IGFBP-2 and -5

<400> SEQUENCE: 10
ggagccgggc ugcggcugct t                                                 21

<210> SEQ ID NO 11
<211> LENGTH: 21
<212> TYPE: DNA
<213> ORGANISM: Artificial Sequence
<220> FEATURE:
<223> OTHER INFORMATION: one strand of RNAi for human IGFBP-2 and -5
```

```
<400> SEQUENCE: 11
gcagccgcag cccggcucct t                                              21

<210> SEQ ID NO 12
<211> LENGTH: 19
<212> TYPE: DNA
<213> ORGANISM: Artificial Sequence
<220> FEATURE:
<223> OTHER INFORMATION: pone strand of RNAi for human IGFBP-2 AND -5

<400> SEQUENCE: 12
cgugcggcgu cuacacctt                                                 19

<210> SEQ ID NO 13
<211> LENGTH: 19
<212> TYPE: DNA
<213> ORGANISM: Artificial Sequence
<220> FEATURE:
<223> OTHER INFORMATION: one strand of RNAi for human IGFBP-2 and -5

<400> SEQUENCE: 13
gguguagacg ccgcacgtt                                                 19

<210> SEQ ID NO 14
<211> LENGTH: 18
<212> TYPE: DNA
<213> ORGANISM: Artificial Sequence
<220> FEATURE:
<223> OTHER INFORMATION: one strand of RNAi for human IGFBP-2 and -5

<400> SEQUENCE: 14
ccaggggcug cgcugctt                                                  18

<210> SEQ ID NO 15
<211> LENGTH: 18
<212> TYPE: DNA
<213> ORGANISM: Artificial Sequence
<220> FEATURE:
<223> OTHER INFORMATION: one strand of RNAi for human IGFBP-2 and -5

<400> SEQUENCE: 15
gcagcgcagc cccuggtt                                                  18
```

METHOD FOR TREATMENT OF CASTRATION-RESISTANT PROSTATE CANCER

FIELD OF THE INVENTION

This application relates to the treatment of castration-resistant prostate cancer (CRPC) that is resistant to androgen-receptor antagonists such as enzalutamide by inhibition of insulin-like growth factor binding protein (IGFBP) 2 and 5.

BACKGROUND OF THE INVENTION

Prostate cancer is a common form of cancer in men worldwide, and in 2008 was the sixth leading cause of cancer death. Initial presentation of prostate cancer is generally androgen-dependent, such that androgen-deprivation therapy, for example through chemical or surgical castration provides a therapeutic benefit. Over time, however, changes to the cancer result in the emergence of androgen-independent cells and relapse and progression of the disease. Various additional therapeutic agents are now available that are focused on the treatment of androgen-independent prostate cancer. Among these therapeutic agents is enzalutamide (previously known as MDV3100), an androgen-receptor antagonist that blocks the androgen receptor. Another drug, ARN-509, operates through competitive AR inhibition, impairing nuclear translocation of the AR, and AR binding to androgen-response elements of DNA.

Not all CRPC is responsive to androgen-receptor antagonists, including enzalutamide, and resistance can develop after a period of treatment. In the case of enzalutamide, this resistance may arise in at least some instances due to a splice-variant that lacks the ligand binding site of the androgen receptor with which enzalutamide interacts.

Bispecific antisense oligonucleotides are known, for example, from U.S. Pat. No. 7,928,082, which is incorporated herein by reference. Bispecific siRNA oligomers are disclosed in U.S. Pat. No. 7,973,017, which is incorporated herein by reference.

One particular bispecific antisense oligonucleotide is known as OGX-225, a second generation antisense oligonucleotide under development by OncoGenex Pharmaceuticals, Inc. OGX-225 has the structure

SEQ ID NO: 1
5'-CAGCAGCCGCAGCCCGGCTC-3'.

In specific known formulations, SEQ ID NO. 1 is in the form of a 20 base phosphorothioate oligonucleotide; 5-10-5 MOE gapmer, 19 sodium salt having the sequence:

DNA (P-thio)
(SEQ ID NO: 2)
5'-$^{Me}$C$\underline{AG}$$^{Me}$C$\underline{AG}$$^{Me}$C$^{Me}$CG$^{Me}$C$\underline{AG}$$^{Me}$C$^{Me}$C$^{Me}$C$\underline{GG}$$^{Me}$C$^{Me}$U$^{Me}$C-3'

Where:
The underlined nucleosides (G, $^{Me}$A and $^{Me}$U) denote 2'-O-(2-methoxyethyl) (2'-MOE) modifications of the ribonucleosides guanosine, 5-methylcytidine, adenosine and 5-methyluridine ($^{Me}$U=T).
G, $^{Me}$C, and A represent the deoxyribonucleosides 2'-deoxyguanosine, 2'-deoxy-5-methylcytidine, and 2'-deoxyadenosine.
The internucleotide linkages are phosphorothioate diesters (nonadecasodium salt).

SUMMARY OF THE INVENTION

The present inventors have found that CRPC cell lines exhibiting resistance to the androgen-receptor antagonist enzaluatamide overexpress one or both of IGFBP-2 or IGFBP-5 when compared to non-resistant cell lines, and that OGX-225 is capable of killing these resistant cells. Thus, in accordance with one aspect of the invention, a method for treatment of prostate cancer is provided in which an agent effective to reduce expression of IGFBP-2 and IGFBP-5 is administered to a patient exhibiting resistance to an androgen-receptor antagonist such as enzalutamide. In a further aspect of the invention, a method for treatment of prostate cancer is provided in which an agent effective to reduce expression of IGFBP-2 and IGFBP-5 is administered to a patient suffering from prostate cancer, and particularly CRPC, concurrently with the administration of androgen-receptor antagonist treatments. Administration of the antisense concurrently with the androgen-receptor antagonist treatment reduces selective pressure towards resistance within the cancer cell population and therefore can delay onset of androgen-receptor antagonist resistance as well as directly providing a therapeutic benefit by killing resistant cells.

DETAILED DESCRIPTION OF THE INVENTION

Definitions

As used in the present application, the term CRPC refers to castrate-resistant prostate cancer and encompasses metastatic CRPC (or mCRPC).

As used in the present application, the term "patient" refers to a human patient.

The term "therapeutic agent" refers to a composition that is administered to the patient in an amount sufficient to achieve a therapeutic effect in non-resistant patients. There is no requirement implied that the agent will be or remain therapeutically effective in any particular patient.

The phrase "effective to reduce expression of IGFBP-2 and IGFBP-5" refers to the ability of an agent to produce a statistically significant reduction in the amount of IGFBP-2 and IGFBP-5 when IGFBP-2 and IGFBP-5 are expressed by treated cells, in this case prostate cancer cells. As discussed below, some resistant cell lines express only one of the two IGFBP's or express them to significantly different extents.

The phrase "concurrently administering" means that first and second therapeutic agents are being administered in a time frame such that the biological activity of the two agents overlaps to at least some extent. In some embodiments, the time period of administration of the first agent overlaps with the time period of administration of the second agent. In others, the two agents are administered sequentially but in close temporal proximity such that the biological effect of the first agent administered persists to at least some extent at the time the second agent is administered.

The term "androgen-receptor antagonist" refers to an active agent that binds to the ligand-binding domain of androgen-receptor as act as an antagonist. Examples of androgen-receptor antagonists are discussed below.

The term "resistant to an androgen-receptor antagonist" or "having androgen-receptor antagonist resistance" means that the CRPC in a particular patient is exhibiting either no therapeutic response, or a therapeutic response that is below expectations based on responses observed in test populations to treatment with the same androgen-receptor antagonist. The phrase "reduced response to androgen-receptor antagonist" means that the patient has previously been treated and provided with therapeutic benefit with the same androgen-receptor antagonist and subsequently becomes resistant to the androgen-receptor antagonist.

The phrase "resistant to enzalutamide" or "having enzalutamide resistance" means that the CRPC in a particular patient is exhibiting either no therapeutic response, or a therapeutic response that is below expectations based on responses observed in test populations to treatment with enzalutamide. The phrase "reduced response to enzalutimade" means that the patient has previously been treated and provided with therapeutic benefit with enzalutamide and subsequently becomes resistant to enzalutamide. This may arise due to a spontaneous F876L mutation in the androgen receptor. Korpal et al., *Cancer Discov.* 2013: 1030-1043 that causes an antagonist to agonist switch.

The term oligonucleotide refers to a short nucleic acid molecule having a total length of 100 bases or less. The nucleic acid molecule may be single stranded or double stranded, and may be DNA, RNA or a mixture DNA and RNA bases. For example, antisense oligonucleotides are single stranded DNA sequences or DNA/RNA gapmers, while siRNA is a duplex of RNA molecules.

In referring to an oligonucleotide that "has the sequence of SEQ ID NO. X" this means that the bases of the oligonucleotide consist of the bases in the recited SEQ ID NO. X, but does not exclude modifications not shown in the sequence listing, for example backbone modifications, derivatization of the bases (for example replacing a base with a methylated form of the same base), locked nucleic acids (LNA) or Isis 2.5 chemistry, "IScET". See U.S. Pat. Nos. 7,399,845; 7,547,684 and 7,666,854 which are incorporated herein by reference.

Agents Effective to Reduce Expression of IGFBP-2 and IGFBP-5

As used in this application, "agents effective to reduce expression of IGFBP-2 and IGFBP-5" refers to sequence-related oligonucleotide therapeutic agents that when introduced to cells expressing IGFBP-2 and IGFBP-5 are capable of reducing expression of both proteins. Sequence-related oligonucleotide therapeutic agents are oligonucleotides that have at most two bases that are not the same as or complementary to the target sequence of the wild type human gene. Thus, aptamers would only fall within the scope of the claims by coincidence and are not generally considered to be sequence-related oligonucleotides.

Figure 1:
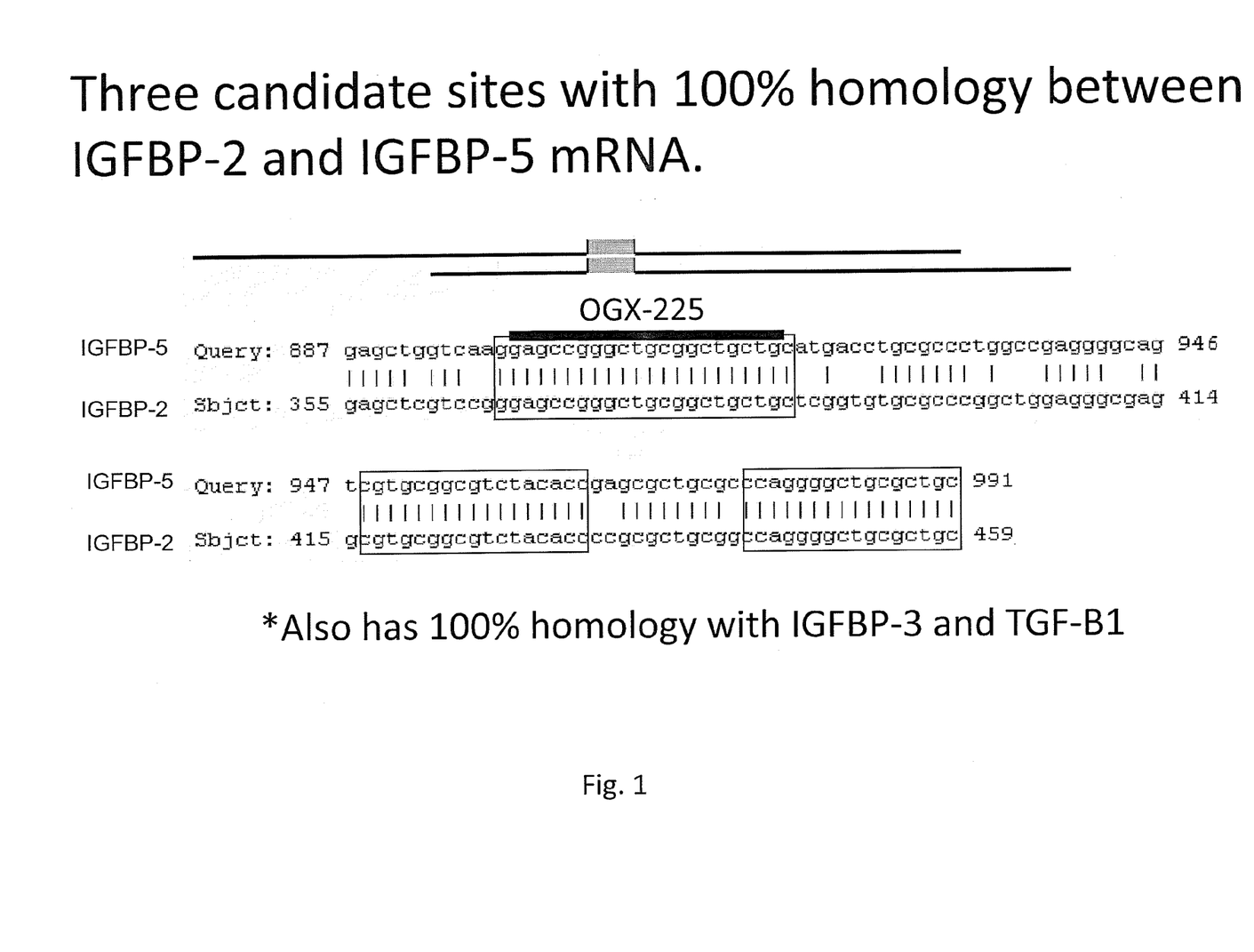
FIG. 1 shows three regions with 100% homology between the sequences of human IGFBP-2 and IGFBP-5 that could be used as bispecific antisense oligonucleotide in accordance with the invention.

A first class of oligonucleotides that can be used as agents to reduce expression of IGFBP-2 and IGFBP-5 are antisense oligonucleotides that are complementary to the coding strand of the IGFBP-2 and IGFBP-5 genes. Suitable antisense oligonucleotides target one of the homologous regions of the human IGFBP-2 and IGFBP-5 genes as illustrated in FIG. 1 and have a length of at least 12 bases. Specific sequences for this purpose include SEQ ID NOs. 1-9.

Antisense oligonucleotides are commonly modified in any of a variety of ways to enhance stability, control clearance rates, reduce toxicity and for other reasons. Any of these modifications may be made to the antisense oligonucleotides for use in the present invention. As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally preferred. In addition, linear compounds may have internal nucleobase complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Internucleoside Linkages (Backbones)

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253;

5,571,799; 5,587,361; 5,194,599; 5,565,555; 5,527,899; 5,721,218; 5,672,697 and 5,625,050, each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

Modified Sugar and Internucleoside Linkages-Mimetics

In other preferred oligonucleotide mimetics, both the sugar and the internucleoside linkage (i.e. the backbone), of the nucleotide units are replaced with novel groups. The nucleobase units are maintained for hybridization with an appropriate target nucleic acid. One such compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

Preferred embodiments of the invention are oligonucleotides with phosphorothioate backbones and oligonucleosides with heteroatom backbones, and in particular —$CH_2$—NH—O—$CH_2$—, —$CH_2$—N($CH_3$)-O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified Sugars

Modified oligonucleotides may also contain one or more substituted sugar moieties. Preferred oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_m$ $CH_3$, $O(CH_2)_nOCH_3$, $O(CH_2)_nNH_2$, $O(CH_2)_nCH_3$, $O(CH_2)_{n}ONH_2$, and $O(CH_2)_nON[(CH_2)_nCH_3]_2$, where n and m are from 1 to about 10. Other preferred oligonucleotides comprise one of the following at the 2' position: $C_1$ to C lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy(2'-O—$CH_2CH_2OCH_3$, also known as 2'-O-(2-methoxyethyl) or 2'-MOE) (Martin et al., Helv. Chim. Acta, 1995, 78, 486-504) i.e., an alkoxyalkoxy group. A further preferred modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—N($CH_3$)$_2$.

Other preferred modifications include 2'-methoxy(2'-O—$CH_3$), 2'-aminopropoxy(2'-$OCH_2CH_2CH_2NH$), 2'-allyl(2'-$CH_2$—CH=$CH_2$), 2'-O-allyl(2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

A further preferred modification of the sugar includes Locked Nucleic Acids (LNAs) in which the 2'-hydroxyl group is linked to the 3' or 4' carbon atom of the sugar ring, thereby forming a bicyclic sugar moiety. The linkage is preferably a methylene (—$CH_2$—)$_n$ group bridging the 2' oxygen atom and the 4' carbon atom wherein n is 1 or 2. LNAs and preparation thereof are described in published International Patent Application Nos. WO 98/39352 and WO 99/14226.

Natural and Modified Nucleobases

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—Ca≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3,4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are particularly useful for increasing the binding affinity of the compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2.degree. C. and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; and 5,681,941, and U.S. Pat. No. 5,750,692, each of which is herein incorporated by reference.

Conjugates

Another modification of the oligonucleotides of the invention involves chemically linking to the oligonucleotide one or more moieties or conjugates that enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenan-thridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, the entire disclosures of which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety. Oligonucleotides of the invention may also be conjugated to active drug substances, for example, aspirin, warfarin, phenylbutazone, ibuprofen, suprofen, fenbufen, ketoprofen, (S)-(+)-pranoprofen, earprofen, dansylsarcosine, 2,3,5-triiodo-benzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic. Oligonucleotide-drug conjugates and their preparation are described in U.S. Pat. No. 6,656,730 which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

Chimeric Compounds

It is not necessary for all positions in a given compound to be uniformly modified, and in fact more than one of the aforementioned modifications may be incorporated in a single compound or even at a single nucleoside within an oligonucleotide.

The present invention also includes antisense compounds that are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, increased stability and/or increased binding affinity for the target nucleic acid. An additional region of the oligonucleotide may serve as a substrate for enzymes capable of cleaving RNA:DNA or RNA:RNA hybrids. By way of example, RNAse H is a cellular endonuclease which cleaves the RNA strand of an RNA:DNA duplex. Activation of RNase H, therefore, results in cleavage of the RNA target, thereby greatly enhancing the efficiency of oligonucleotide-mediated inhibition of gene expression. The cleavage of RNA:RNA hybrids can, in like fashion, be accomplished through the actions of endoribonucleases, such as RNAseL which cleaves both cellular and viral RNA. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety.

Stability can be increased through the use of non-naturally occurring nucleic acid bases such as those disclosed in U.S. Pat. Nos. 6,268,490, 6,770,748, 7,399,845; 7,547,684; and 7,666,854, for example.

A second class of oligonucleotides that can be used as agents to reduce expression of IGFBP-2 and IGFBP-5 are small interfering RNA (siRNA), sometimes known as short interfering RNA or silencing RNA. siRNA are double-stranded RNA molecules that are 20-25 base pairs in length. siRNA may be modified to enhance stability as discussed above. In particular, 2'-methoxy(2'-0Me) and 2'-fluoro (2'-F) modifications are known to improve stability, specificity or immunogenic properties. siRNA modified with 2'-O-benzyl, and 2'-O-methyl-4-pyridine (2'-O—CH2Py(4) may also be employed to enhance potency. Kenski et al, *Molecular Therapy Nucleic Acids* (2012) 1.

Specific siRNA sequences known to be effective at reducing expression of both IGFBP-2 and IGFBP-5 cells are disclosed in U.S. Pat. No. 8,252,918, which is incorporated herein by reference. These sequences are listed herein as SEQ ID NOS. 10 to 15.

In the methods of the invention, it is advantageous to use agents that reduce expression of both IGFBP-2 and IGFBP-5 because the inventors have found that prostate cancers cells may overexpress either or in some cases both of these proteins. By using a bispecific reagent, prior determination of the actual nature of a patient's tumor is not required.

Androgen-Receptor Antagonists that Bind to the Ligand Binding Domain of Androgen-Receptor The present invention teaches the use of an androgen-receptor antagonist that binds to the ligand binding domain of androgen receptor.

One class of compounds that can be used as androgen-receptor antagonists are diarylthiohydantoins such as enzalutamide. (systematic (IUPAC) name: 4-(3-(4-Cyano-3-(trifluoromethyl)phenyl)-5,5-dimethyl-4-oxo-2-thioxoimidazolidin-1-yl)-2-fluoro-N-methylbenzamide); RD162 (4-[7-(4-Cyano-3-trifluoromethyl-phenyl)-8-oxo-6-thioxo-5,7-diaza-spiro[3.4]oct-5-yl]-2-fluoro-N-methyl-benzamide); and ARN-509 (4-(7-(6-cyano-5-(trifluoromethyl)pyridin-3-yl)-8-oxo-6-thioxo-5,7-diazaspiro[3.4]octan-5-yl)-2-fluoro-N-methylbenzamide). See Tran et al., Science. 2009 May 8; 324(5928): 787-790; Clegg et al. ARN-509: a novel antiandrogen for prostate cancer treatment. Cancer Res. 2012, 72(6), 1494-1503. Androgen receptor antagonists of this type have been shown to limit or have no effect upon nuclear translocation of androgen receptor, in contrast to compounds such as bicalutamide that stimulate androgen translocation. Thus, in one aspect, the androgen receptor antagonist is one that does not statistically enhance nuclear translocation.

| COMPOUND NAME | STRUCTURE | ALTERNATE NAMES |
|---|---|---|
| Enzalutamide | | Xtandi, MDV3100, Chemical name: 4-(3-(4-Cyano-3-(trifluoromethyl)phenyl)-5,5-dimethyl-4-oxo-2-thioxoimidazolidin-1-yl)-2-fluoro-N-methylbenzamide, CAS number 915087-33-1 |
| ARN-509 | | Benzamide, 4-[7-[6-cyano-5-(trifluoromethyl)-3-pyridinyl]-8-oxo-6-thioxo-5,7-diazaspiro[3.4]oct-5-yl]-2-fluoro-N-methyl- - |

Bicalutamide, nilutamide and flutamide are "first generation" anti-androgens that may also be androgen receptor antagonists in the context of the present invention. PF 998425 (Li et al (2008) Rational design and synthesis of 4-((1R,2R)-2-hydroxycyclohexyl)-2(trifluoromethyl)benzonitrile (PF-998425), a novel, nonsteroidal androgen receptor antagonist devoid of phototoxicity for dermatological indications. J. Med. Chem. 51 7010.) is a further androgen receptor antagonist within the scope of the invention.

As shown below, these compound share are arylpropionamides or analogs thereof (nilutamide is a nitroaromatic hydantoin analog of flutamide). Moreover, in these structures, the benzene ring, is substituted with a trifluromethyl group in 2-position and a cyano or nitro group in the 3-position.

| COMPOUND NAME | STRUCTURE | ALTERNATE NAMES |
|---|---|---|
| Bicalutamide | | Casodex, ICI 176,334<br>Chemical Name: N-[4-Cyano-3-(trifluoromethyl)phenyl]-3-[(4-fluorophenyl)sulfonyl]-2-hydroxy-2-methyl propanamide |
| Flutamide | | Alternative Name: SCH 13521<br>Chemical Name: 2-Methyl-N-(4-nitro-3-[trifluoromethyl]phenyl)propanamide |
| Nilutamide | | Alternative Name: RU 23908<br>Chemical Name: 5,5-Dimethyl-3-[4-nitro-3-(trifluoromethyl)phenyl]-2,4-imidazolidinedione |
| PF 998425 | | Chemical Name: 4-((1R,2R)-2-Hydroxycyclohexyl)-2-(trifluoromethyl) benzonitrile |

Other compounds that are considered androgen-receptor antagonists within the scope of the invention are shown below:

| Name of compound | Structure | Company |
|---|---|---|
| RU58642 | | Roussel-Uclaf SA |

| Name of compound | Structure | Company |
|---|---|---|
| LG120907 | | Ligand Pharmaceuticals |
| LG105 | | Ligand Pharmaceuticals |
| BMS-641988 | | Bristol-Myers Squibb |
| CH5137291 | | Chugai Pharmaceutical Co. Ltd. |

Administration of Therapeutic Agents

The therapeutic agents used in the methods of the invention can be administered by appropriate methods known for use with the particular agent, For example, in the case of oligonucleotides, the antisense can be administered, systemically by intravenous injection, or intra-tumorally in the case of a localized tumor. The amount of oligonucleotide is dependent on the body size of the patient, the frequency of dosing and observed toxicity but will in general fall in the range of 10 mg to 1000 mg per treatment. Appropriate adjuvants consistent with the oligonucleotide may also be employed, including buffers, lipid-encapsulation, tissue/cancer-specific targeted carriers and the like Androgen-receptor antagonists are used at standard approved dosages levels, and are commonly formulated for oral administrations. By way of example only, Table 1 shows exemplary dosages for various androgen-receptor antagonists.

TABLE 1

| Antagonist | Dosage (human patient) |
|---|---|
| bicalutamide | 50-150 mg. day |
| enzalutamide | 160 mg daily |
| ARN-509 | 240 mg daily |
| flutamide | 750 mg every 8 hours |
| nilutamide | 150-300 mg daily |

Experimental Support

Tests were performed on androgen sensitive cells line (LNCaP), castrate resistant, enzalutamide-sensitive prostate cancer cell lines V16A and V16D, which were derived from LNCaP cells grown in castrated nude, Matsumoto, H.; Yamamoto, Y.; Shiota, M.; et al. Cancer Res. (2013) 73(16): 5206-17 and Kuruma, H; Matsumoto, H.; Shiota, M. et al. Mol Cancer Ther (2013) 12(5): 567-76; and castrate resistant, enzalutamide-resistant prostate cancer cell lines MR42D, MR49C, and MR49F which were derived from LNCaP cells grown in castrated nude mice treated with enzalutamide at 10 mg/kg PO daily. BPH-1 is an immortal, benign prostatic hyperplasia cell line (Hayward S W, Dahiya R, Cunha G R, et al. (1995). In Vitro Cell Dev Biol Anim 31: 14-24).

Standard control cell lines were DU145 (HTB-81, ATCC) and C4-2. C4-2 is a castrate resistant-derivative of LNCaP (Thalmann G N, Anezinis P E, Chang S M, et al. (1994) Cancer Res 54:2577-2581).

H660 is a neuroendocrine prostate cancer cell line originally thought to be a small cell lung cancer derived. Carney D N, Gazdar A F, Bepler G, et al. Cancer Res. (1985)45: 2913-2923.

OGX-225 (SEQ ID NO. 2) was used as an agent that reduces expression of IGFBP-2 and IGFBP-5. Enzalutamide was used as the androgen receptor antagonist.

IGFBP-2 and IGFBP-5 expression was determined in various cell lines prior to treatment either agent. As shown in Table 2, substantial IGFBP-2 expression was observed in four of the five cell lines while IGFBP-5 expression was lower (expressed as mRNA expression per $10^6$ transcripts).

TABLE 2

|        | LNCaP | DU145 | C4-2  | V16A   | V16D   | MR42D  | MR49C  | MR49F  |
|--------|-------|-------|-------|--------|--------|--------|--------|--------|
| IGFBP2 | 32.54 | 0.17  | 64.61 | 116.75 | 176.92 | 183.4  | 153.75 | 157.02 |
| IGFBP5 | 0.73  | 0.04  | 0.21  | 2.66   | 1.11   | 266.63 | 30.18  | 6.05   |

Figure 2:
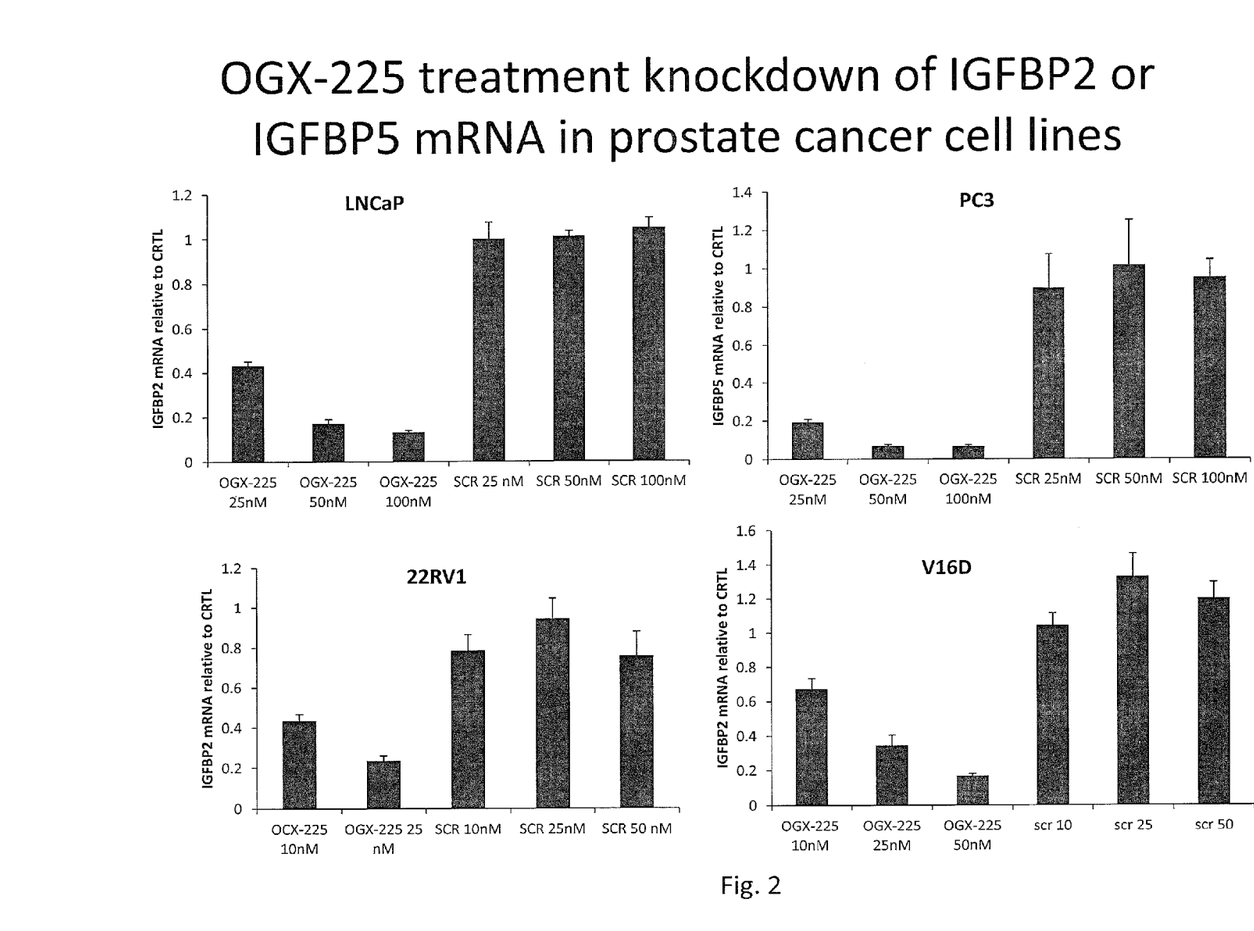
FIG. 2 shows reduction of IGFBP-2 or IGFBP-5 in various prostate cancer cell lines.

Conversely, PC3 cells express IGFBP-5 but not IGFBP-2. OGX-225 was shown to be able to reduce the amount of the predominant IGFBP in a dose dependent manner when added to cells lines in vitro at concentrations of 10 nM to 100 nM (FIG. 2)

Figure 3:
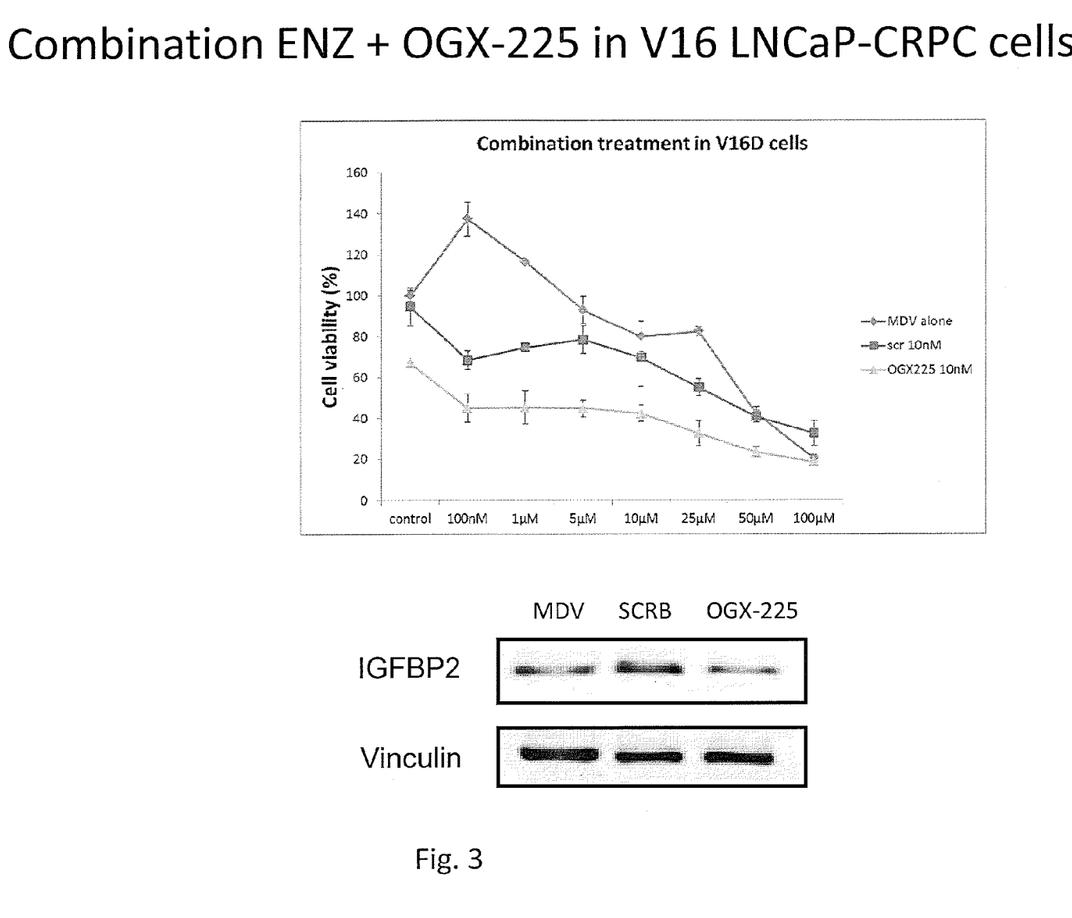
FIG. 3 shows cells viability for V16 castrate-resistant LNCaP-derived cells treated with combinations of enzalutamide and OGX-225.

Cell viability was determined in V16 castration-resistant LNCaP-derived cells when treated with varying concentrations of enzalutamide (MDV) alone or in combination with a scrambled antisense control (10 nM) or OGX-225 (10 nM). The results are shown in FIG. 3. As shown, low levels of cell viability are achieved by the combination of enzalutamide and OGX-225 at much lower enzalutamide levels than required for use of enzalutamide alone. Reduction in the IGFBP-2 level in the samples treated with OGX-225 was confirmed.

Figure 4:
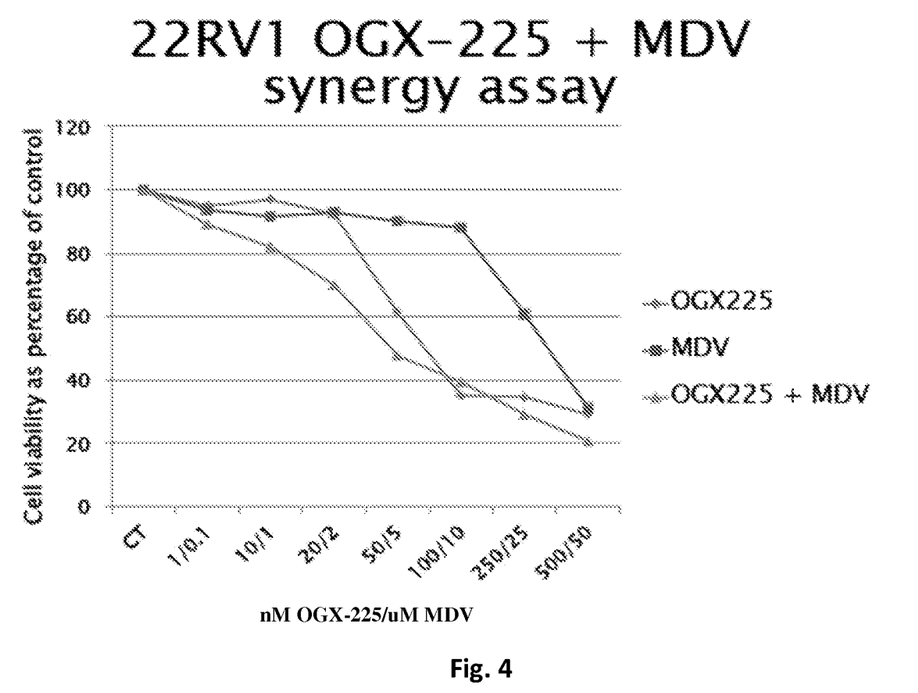
FIG. 4 shows cell viability for 22RV1 cells treated with combinations of OGX-225 and enzalutamide.

Cell viability was determined I 22RV1 cells after treatment with OGX-225 or enzalutaimide (MDV) alone or in combination. As shown in FIG. 4 the combination therapy reduced cell viability at much lower concentrations than required for either agent alone. Combination Index determination showed synergy for the combination at dosages of ED50 and ED75.

Figure 5A:
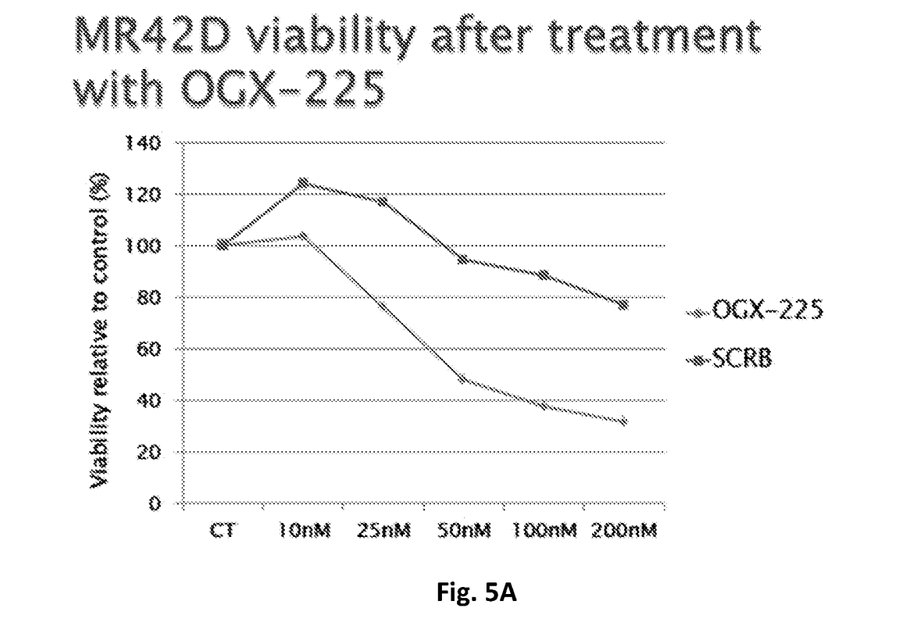
FIGS. 5A and B show cell viability in enzalutamide resistant cell lines MR42D and MR42F, respectively.
Figure 5B:
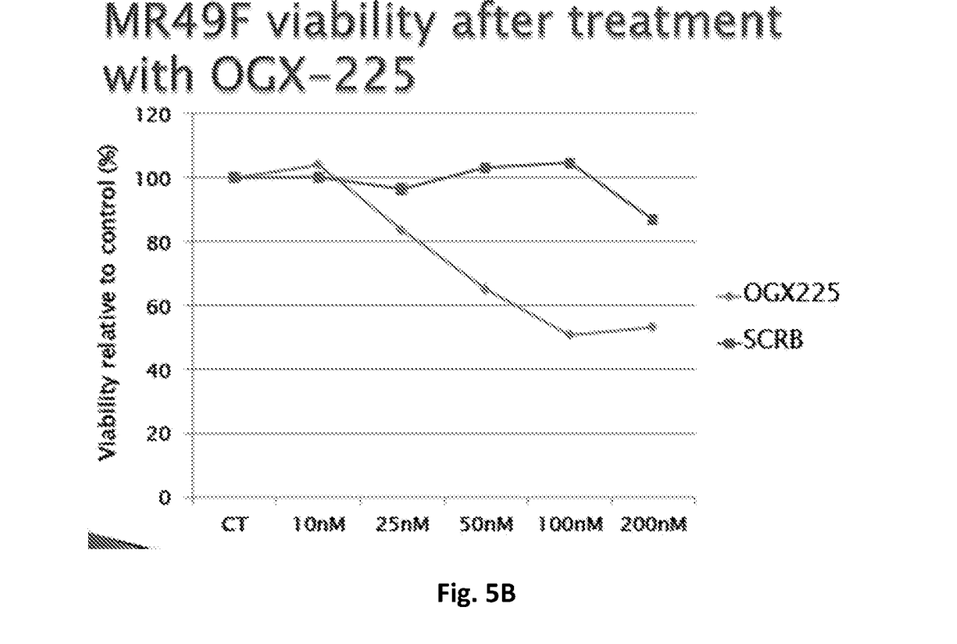

FIGS. 5A and B show cells viability in enzalutamide resistant cell lines MR42D and MR42F, respectively, As shown, in each case OGX-255 was able to substantially reduce the viability as compared to a scrambled control.

EXEMPLIFICATION

Patient is treated with antiandrogen (enzalutamide, bicalutamide, ARN-509, etc.) orally, and then given an intravenous OGX-225 infusion. These steps are repeated as many times as necessary until the patient exhibits no further symptoms, or until staging testing yields the desired negative or static result.

The invention claimed is:

1. A method for treatment of a patient having a cancer exhibiting resistance to an androgen-receptor antagonist comprising administering to the patient an amount of a sequence-related oligonucleotide therapeutic agent that reduces expression of IGFBP-2 and IGFBP-5.

2. The method of claim 1 wherein the androgen-receptor antagonist impairs nuclear translocation of androgen-receptor.

3. The method of claim 1, wherein the androgen-receptor antagonist is a diarylthiohydantoin.

4. The method of claim 3, wherein the androgen-receptor antagonist is enzalutamide.

5. The method of claim 4, wherein the agent that reduces expression of IGFBP-2 and IGFBP-5 is a bispecific antisense oligonucleotide.

6. The method of claim 5, wherein the agent has the sequence of SEQ ID NO.: 1.

7. The method of claim 5, wherein the agent is OGX-225 (SEQ ID NO. 2).

8. The method of claim 4, wherein the agent that reduces expression of IGFBP-2 and IGFBP-5 is an siRNA.

9. The method of claim 8, wherein the siRNA is an RNA duplex of two complementary RNA strands in which one of the strands has the sequence of SEQ ID NO.: 10.

10. The method of claim 1, wherein the agent that reduces expression of IGFBP-2 and IGFBP-5 is a bispecific antisense oligonucleotide.

11. The method of claim 10, wherein the agent has the sequence of SEQ ID NO.: 1.

12. The method of claim 10, wherein the agent is OGX-225 (SEQ ID NO. 2).

13. The method of claim 1, wherein the agent that reduces expression of IGFBP-2 and IGFBP-5 is an siRNA.

14. The method of claim 13, wherein the siRNA is an RNA duplex of two complementary RNA strands in which one of the strands has the sequence of SEQ ID NO.: 10.

15. The method of claim 1, wherein the cancer exhibits a reduced response to the androgen-receptor antagonist.

16. A method for treatment of a patient having prostate cancer comprising concurrently administering to the patient
(a) a first therapeutic agent that is an androgen-receptor antagonist that binds to the ligand binding domain of an androgen-receptor; and (b) a second therapeutic agent that is a sequence-related oligonucleotide therapeutic agent that reduces expression of IGFBP-2 and IGFBP-5, wherein the prostate cancer is castrate-resistant prostate cancer.

17. The method of claim 16, wherein the prostate cancer is a metastatic castrate-resistant prostate cancer.

18. The method of claim 16, wherein the first therapeutic agent is an androgen-receptor antagonist that impairs nuclear translocation of an androgen-receptor.

19. The method of claim 18, wherein the androgen-receptor antagonist is a diarylthiohydantoin.

20. The method of claim 16, wherein the agent that reduces expression of IGFBP-2 and IGFBP-5 is a bispecific antisense oligonucleotide.

21. The method of claim 16, wherein the agent that reduces expression of IGFBP-2 and IGFBP-5 is an siRNA.

22. The method of claim 21, wherein the siRNA is an RNA duplex of two complementary RNA strands in which one of the strands has the sequence of SEQ ID NO.: 10.

23. The method of claim 20, wherein the bispecific antisense oligonucleotide is SEQ ID NO.: 1 or OGX-225 (SEQ ID NO. 2).

24. The method of claim 19, wherein the androgen-receptor antagonist is a enzalutamide.

* * * * *